(12) United States Patent
DiTrolio

(10) Patent No.: US 8,389,023 B2
(45) Date of Patent: *Mar. 5, 2013

(54) CHEMOABLATION OF TISSUE USING BIODEGRADABLE, SOLID SALT DOSAGE FORMS

(75) Inventor: Joseph V. DiTrolio, Roseland, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/241,952

(22) Filed: Sep. 23, 2011

(65) Prior Publication Data

US 2012/0016338 A1    Jan. 19, 2012

Related U.S. Application Data

(63) Continuation of application No. 11/810,075, filed on Jun. 4, 2007, now Pat. No. 8,057,827, which is a continuation of application No. 10/940,589, filed on Sep. 14, 2004, now Pat. No. 7,226,622.

(60) Provisional application No. 60/503,954, filed on Sep. 18, 2003.

(51) Int. Cl.
| | |
|---|---|
| *A61K 33/14* | (2006.01) |
| *A61B 17/42* | (2006.01) |
| *A61M 5/178* | (2006.01) |
| *A61M 31/00* | (2006.01) |
| *A61M 25/06* | (2006.01) |
| *A61M 5/315* | (2006.01) |

(52) U.S. Cl. ............... 424/680; 604/28; 604/36; 604/38; 604/44; 604/48; 604/57; 604/59; 604/60; 604/62; 604/64; 604/264; 604/272; 606/272

(58) Field of Classification Search ........................ None
See application file for complete search history.

(56) References Cited

U.S. PATENT DOCUMENTS

| | | | | |
|---|---|---|---|---|
| 3,717,097 | A | * | 2/1973 | Wronka et al. ............... 102/334 |
| 3,744,493 | A | * | 7/1973 | Booher et al. ................. 604/62 |
| 4,461,280 | A | | 7/1984 | Baumgartner |
| 4,588,395 | A | | 5/1986 | Lemelson |
| 4,943,579 | A | | 7/1990 | Vishnuvajjala et al. |
| 5,106,742 | A | | 4/1992 | Wall et al. |
| 5,846,565 | A | | 12/1998 | Brem et al. |
| 5,874,098 | A | * | 2/1999 | Stevens et al. ............... 424/408 |
| 5,891,457 | A | * | 4/1999 | Neuwirth ...................... 424/430 |
| 6,162,203 | A | | 12/2000 | Haaga |
| 6,168,777 | B1 | | 1/2001 | Greff et al. |
| 6,231,591 | B1 | | 5/2001 | Desai |
| 6,277,391 | B1 | | 8/2001 | Seo et al. |
| 6,461,296 | B1 | | 10/2002 | Desai |
| 7,226,622 | B2 | | 6/2007 | DiTrolio |
| 2002/0010150 | A1 | | 1/2002 | Cortese et al. |
| 2002/0082610 | A1 | | 6/2002 | Cioanta et al. |

FOREIGN PATENT DOCUMENTS

| | | |
|---|---|---|
| GB | 2 123 818 A | 2/1984 |
| WO | 99/59650 | 11/1999 |
| WO | 03/005889 A2 | 1/2003 |
| WO | 03/043606 A1 | 5/2003 |

OTHER PUBLICATIONS

Hyperkalemia [online] retrieved from: http://en.wikipedia.org/wiki/Hyperkalemia; Jun. 18, 2012; 7 pages.*
Francium Element Facts [online] retrieved from: http://www.chemicool.com/elements/francium.html; Jun. 17, 2012; 6 pages.*
Solubility Rules [online] retrieved from: http://www.chem.sc.edu/analytical/chem111/backup_080707/solubility.html on Jun. 17, 2012; Sep. 2001, 2 pages.*
Weekly World News, Feb. 23, 1999; p. 14. 2 pages.*
Bustos-Lopez, Fertility and Sterility, 1998, 69(1) 155-160.
Joseph V. DiTrolio, "A Novel Treatment for BPH: Transurethral Ethoanol Ablation of the Prostate (TEAP)," slide presentation, 20th World Congress on Endourology & Shockwave, Sep. 20, 2002. Genoa, Italy, 3 pp.
Hoey et al, Transurethral Prostate Ablation Using Saline-Liquid Electrode Introduced Via Flexible Cystoscope, J Endourol, Oct. 1998; 12(5): 461-8.
Russell (The nutrition and health dictionary, 1995 Jones & Bartlett p. 114).
Maupoei (Osmotic dehydration & vacuum impregnation, 2001, CRC Press, p. 155).
Goldberg et al. (Radiology 2001, 219(1), pp. 157-165).

* cited by examiner

*Primary Examiner* — Ernst Arnold
(74) *Attorney, Agent, or Firm* — Mayer & Williams PC; David B. Bonham; Keum J. Park

(57) ABSTRACT

Novel methods for the chemical ablation of tissue (e.g. prostatic tissue) are described. These methods include the steps of: (a) providing one or more solid salt dosage form comprising 50-100% w/w salt; and (b) inserting one or more of such solid salt dosage forms into the tissue. The solid salt dosage form is optionally inserted into the tissue under real-time ultrasonic observation. An advantage of the present invention is its ability to eliminate toxic byproducts. For example, where NaCl-based solid salt dosage forms are used to effect localized chemical ablation, the concentration is ultimately reduced to the level of normal saline (i.e., about 0.9%) upon absorption by the body of the subject being treated.

26 Claims, 1 Drawing Sheet

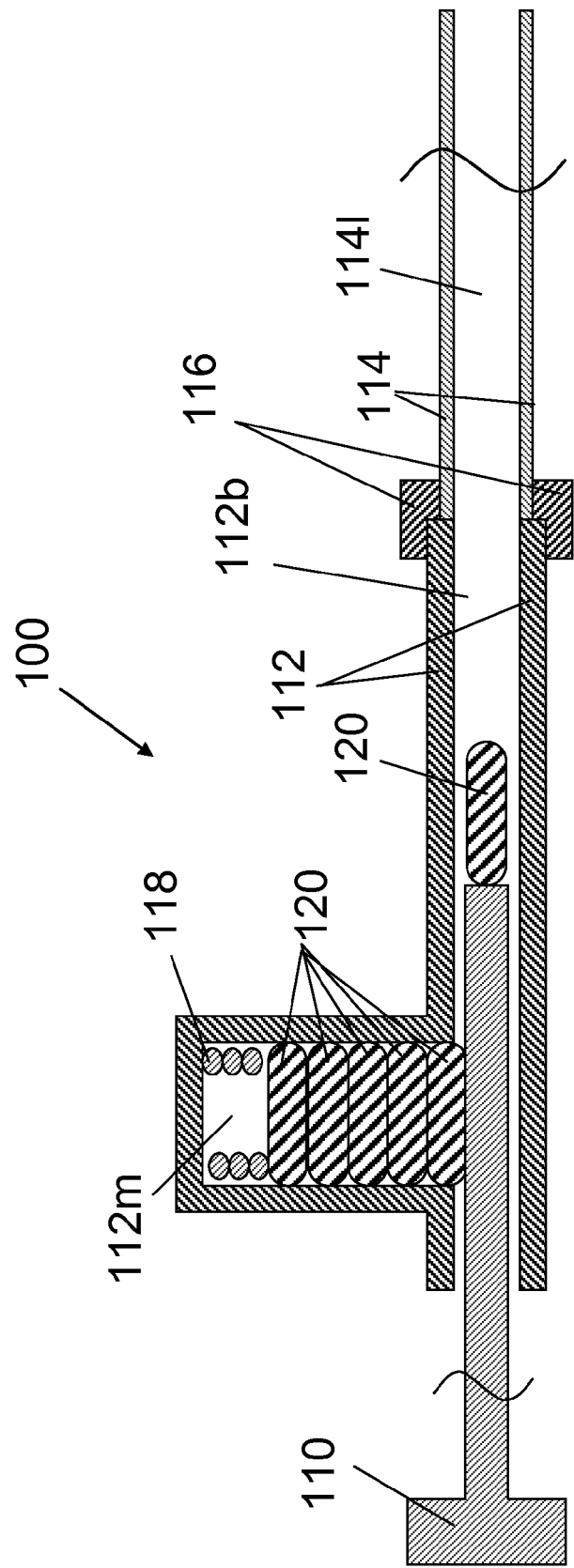

CHEMOABLATION OF TISSUE USING BIODEGRADABLE, SOLID SALT DOSAGE FORMS

STATEMENT OF RELATED APPLICATION

This application is a continuation of U.S. patent application Ser. No. 11/810,075, filed Jun. 4, 2007, entitled "Chemoablation Of Tissue Using Biodegradable, Solid State Dosage Forms," now U.S. Pat. No. 8,057,827, which is a continuation of U.S. patent application Ser. No. 10/940,589, filed Sep. 14, 2004, entitled "Chemoablation Of Tissue Using Biodegradable, Solid State Dosage Forms," now U.S. Pat. No. 7,226,622 which claims the benefit of priority to U.S. provisional patent application Ser. No. 60/503,954, filed Sep. 18, 2003. All of the prior applications are incorporated herein by reference in their entireties.

FIELD OF THE INVENTION

The present invention relates to methods for chemoablation of tissue. More particularly, the present invention relates to the insertion of solid salt dosage forms into tissue, such as prostate tissue, which leads to the chemoablation of the tissue.

BACKGROUND OF THE INVENTION

Benign prostatic hypertrophy (BPH) is an age related, natural growth of the prostate, which over time increases the resistance offered by the prostatic gland to the free flow of urine from the bladder to the urethra. The bladder has the ability to contract and generate a voiding pressure, which decreases as the bladder empties. At the point where prostatic resistance is greater than the pressure generated by the bladder, the bladder ceases to evacuate more urine.

In general, the goal of BPH treatment has been to reduce prostatic urethral resistance, primarily by medical management, for example, by administering an alpha blockade or prostatic volume reducer, and secondarily by surgical intervention, for example, by resorting to prostatic resection, laser vaporization, thermal destruction, or injected chemical destruction.

Hence, the ability to remove prostate tissue via volume depletion is a cornerstone of BPH treatment. Chemical ablation, where utilized, will ideally have the ability to destroy tissue and become tissue neutral upon completion of its function.

SUMMARY OF THE INVENTION

These and other needs and challenges are met by the present invention.

Accordingly, one aspect of the present invention is directed to novel methods for the chemical ablation of tissue, such as prostatic tissue. These methods include the steps of: (a) providing one or more solid salt dosage forms comprising salt in an amount sufficient to achieve chemical ablation, typically an amount of 10-100%, more typically 50-100% w/w salt (e.g., sodium chloride pellets); and (b) inserting the one or more solid salt dosage forms into tissue. In certain beneficial embodiments, the solid salt dosage forms are inserted into the tissue under real-time ultrasonic observation.

Another aspect of the presenting invention is directed to an apparatus for the insertion of the above solid salt dosage forms into tissue. The apparatus includes: (a) a flexible, semi-rigid, or rigid shaft having a longitudinal lumen; and (b) a flexible, semi-rigid, or rigid pushing member for advancing the dosage forms through the lumen of the shaft, and into tissue. Optionally, a secondary obturator with a sharpened tip may be used initially in place of the pushing member within the sheath to place the sheath into tissue prior to the loading and advancing of the dosage forms with the pushing member. A further option includes the use of a magazine which is adapted to hold a plurality of the solid salt dosage forms and which has an outlet to the lumen of the shaft. The pushing member, in this embodiment is used to advance the dosage forms from a position proximal to the magazine, through the lumen of the shaft, into tissue.

One advantage of the present invention is its simplicity. For example, in the treatment of BPH, the present invention provides a method that allows for office-based chemical ablation of prostatic tissue, in which solid salt dosage forms (e.g., salt pellets) can be placed into the prostate transrectally under ultrasound guidance.

Another advantage of the present invention is its lack of toxic byproducts. For example, in some embodiments, the present invention employs biodegradable NaCl-based solid salt dosage forms (e.g. salt pellets) to effect localized chemical ablation. Although initially toxic, upon absorption by the body of the subject being treated, the concentration is reduced to the level of normal saline (i.e., about 0.9%).

These and other embodiments and advantages of the present invention will become immediately apparent to those of ordinary skill in the art upon review of the Detailed Description to follow.

BRIEF DESCRIPTION OF THE DRAWING

FIG. 1 is a schematic, cross-sectional view of a device for delivering solid salt dosage forms, in accordance with an embodiment of the present invention.

DETAILED DESCRIPTION OF THE INVENTION

A first aspect of the present invention is directed to methods for the chemical ablation of living tissue. These methods are carried out using solid salt dosage forms, which comprise 50-100% w/w salt, more typically 95-100% salt. Preferred salts for the practice of the present invention are salts formed from alkali metal halides, for example, salts of any combination of (a) Li, Na, K, Rb or Cs and (b) F, Cl, Br or I. The most preferred salt for the practice of the present invention is NaCl. NaCl is preferred for a number of reasons, including the fact that it is a common, naturally occurring chemical, which if supplied in high enough concentration will cause chemical ablation. Once absorbed by the body of the subject being treated, however, the concentration is reduced to the level of normal saline (i.e., about 0.9%) and is no longer toxic.

In certain embodiments, the solid salt dosage forms of the present invention are provided with one or more polymeric coatings.

The methods of the present invention are typically carried out by inserting the above-described solid salt dosage forms into living tissue. For example, in certain embodiments of the invention, the solid salt dosage forms are inserted by pushing the dosage forms through a hollow shaft and into tissue using a pushing member (e.g., an obturator). In general, the hollow shaft, the pushing member, or both can be provided with a sharp tip to allow penetration into the tissue of interest.

In order to assist with the proper placement of the solid salt dosage forms, insertion is optionally conducted with the aid of real-time ultrasonic observation, for example, using commercially available ultrasonic probes.

Subjects for the procedures of the present invention include vertebrate subjects, typically mammalian subjects, and more typically human subjects.

Examples of tissue for treatment in accordance with the present invention include prostatic tissue, kidney tissue, liver tissue, bladder tissue, or any other organ or entity confined by a capsular membrane, preferably prostatic tissue. The treated tissue may comprise benign tumor tissue or malignant tumor tissue. For example, disease states for which the treatment may be useful include, BPH, prostate cancer, prostititis, any other disease states occurring within a capsular membrane-confined organ. The solid salt dosage forms are inserted by any of a variety of routes, including transabdominal, transperineal, transcutaneous, transurethral, and transrectal routes of insertion. Other routes may be suitable depending on the application and location of tissue, which ensures access through the capsular membrane. Where prostatic tissue is to be treated, transperineal, transurethral, and transrectal routes are typically used, with transrectal administration being particularly beneficial.

In certain embodiments, tissue ablation is conducted by inserting a plurality of small dosage forms into the tissue of interest at various locations. Small salt pellets will destroy tissue that is in close proximity. However, due to cumulative effects, a plurality of well placed small pellets can destroy a substantial amount of tissue, even though each pellet may individually destroy only a small amount of tissue.

For example, in the case of benign prostatic hypertrophy treatment, between 2 and 20 NaCl pellets having volumes ranging 1 $mm^3$ to 15 $mm^3$ can be inserted into each side of the prostate, leading to substantial reductions in prostatic volume and thereby obstruction caused by the prostate tissue.

FIG. 1 is a schematic cross-sectional illustration of one apparatus, generally designated by the numeral 100, which can be used for the insertion of multiple solid salt dosage forms into tissue. The apparatus of FIG. 1 includes a housing 112, which contains a magazine 112m and a barrel 112b. A flexible, semi-rigid, or rigid shaft 114 having a longitudinal lumen 114l is attached to the barrel 112b of housing 112 via locking mechanism 116. The magazine 112m contains a plurality of solid salt dosage forms 120, which are urged through the magazine outlet and into the barrel 112b via an urging member 118 (illustrated as a spring). Once in the barrel 112b, pushing member 110 (e.g., an obturator) is used to advance the dosage form 120 down the barrel 112b and into the lumen 114l of the flexible, semi-rigid or rigid shaft 114, for ultimate delivery into tissue (not shown).

EXAMPLE

According to one specific embodiment of the invention for use in the treatment of BPH, salt pellets are introduced into the prostate with the aid of a transrectal ultrasound (TRUS) probe having a snap-on needle guide, such as those that are presently used in connection with prostatic biopsies—a procedure well known to all urologists. For patient comfort, local anesthesia is typically applied, for instance, transrectal application of a 2% xylocaine jelly.

The TRUS probe with snap-on guide is supplemented by the following: (a) a 18-gauge hollow-core semi-rigid plastic sheath with a longitudinal lumen having a diameter slightly greater than 1 mm, and (b) a semi-rigid introductory obturator, dimensioned to allow advancement through the longitudinal lumen of the hollow sheath, and (c) about 1 mm$\emptyset$ about 5 mm length NaCl pellets (having a volume of about 4 $mm^3$), which are also dimensioned for advancement through the longitudinal lumen of the hollow sheath.

The semi-rigid sheath having a blunt end in combination with a piercing obturator having a sharpened tip, (or the sheath alone having a sharpened tip capable of piercing tissue), is inserted through the ultrasound needle guide under live ultrasound observation, whereupon the sheath/piercing obturator combination (or sharpened sheath alone) is used to pierce the prostate at the desired location, typically at a safe distance from the urethra, prostatic capsule or sphincter. Positioning of the sheath allows for the placement of one or more pellets into the prostatic tissue. For this purpose, each pellet is pre-loaded in the sheath prior to insertion whereupon a blunt-ended obturator is inserted into the end of the sheath outside the body in order to advance the pellet down the longitudinal lumen of the semi-rigid 18 gauge sheath and into the prostate tissue. In the case where a piercing obturator is used, it is removed from the sheath after positioning and prior to loading of the pellets. Alternatively, a magazine, as depicted and described with respect to FIG. 1 can be used to load a series of pellets into the sheath.

Using techniques like that described above, each of the above pellets (i.e., 1 mm$\emptyset$×5 mm length NaCl pellets) has been shown to create a zone of necrosis approximately 5 mm beyond the pellets in all directions. When evenly dispersed in adequate numbers, their cumulative tissue destruction will necrose enough prostatic tissue to relieve the obstruction to urinary outflow. A range of pellets (e.g., 20 to 60) may be inserted into each lobe of the prostate. This number may vary up or down depending on different parameters, for example, prostate size, configuration and makeup of the pellet, size of desired treatment zone, etc. Typically from 30 to 40 pellets are inserted into each lobe of the prostate.

After insertion, dissolution of the pellets typically occurs over a period of hours, which may range up to one week, and more typically from about 4 to 24 hours, although dissolution can be accelerated by transrectal vibration or slowed down by coating the pellet with a polymer.

Hence, the present inventor has found that alkali metal halide salts, such as NaCl, which are common, naturally occurring chemicals, will cause chemical ablation if supplied in sufficiently high concentration. Once diluted (eventually to the level of normal saline, i.e., about 0.9%), however, the salt is not longer toxic.

The present inventor has also established a tissue ablation procedure which can be conducted in an office-setting, thereby greatly reducing the cost and inconvenience of the procedure.

Although various embodiments are specifically illustrated and described herein, it will be appreciated that modifications and variations of the present invention are covered by the above teachings without departing from the spirit and intended scope of the invention.

The invention claimed is:

1. A method for the chemical ablation of prostate tissue in a patient in need of ablation, said method comprising: (a) providing a solid salt dosage form comprising 50-100% w/w salt; and (b) inserting said solid salt dosage form into said prostate tissue in a number sufficient to achieve chemical ablation.

2. The method of claim 1, wherein said salt is an alkali metal halide salt.

3. The method of claim 1, wherein said salt is sodium chloride.

4. The method of claim 1, wherein said solid salt dosage form further comprises a polymer coating.

5. The method of claim 1, wherein said solid salt dosage form is injected into said prostate tissue under real-time ultrasonic observation.

6. The method of claim 1, wherein said solid salt dosage form is inserted into said prostate tissue by pushing said dosage form through a hollow sheath.

7. The method of claim 1, wherein said tissue is prostate tissue displaying benign prostatic hypertrophy.

8. The method of claim 1, wherein said tissue is prostate tissue displaying prostate cancer.

9. The method of claim 7, wherein said salt is an alkali metal halide salt.

10. The method of claim 7, wherein said salt is sodium chloride.

11. The method of claim 7, wherein said solid salt dosage form is injected into said prostate tissue under real-time ultrasonic observation.

12. The method of claim 7, wherein said solid salt dosage form is inserted into said prostate tissue by pushing said dosage form through a hollow sheath.

13. The method of claim 7, wherein a plurality of said dosage forms are inserted into said prostate tissue.

14. The method of claim 13, wherein said dosage form is a pellet ranging in volume from 0.5 mm$^3$ to 25 mm$^3$.

15. The method of claim 7, wherein said solid salt dosage form is transrectally inserted into said prostate tissue.

16. The method of claim 7, wherein said solid salt dosage form is transperineally inserted into said prostate tissue.

17. The method of claim 7, wherein said solid salt dosage form is transuretherally inserted into said prostate tissue.

18. The method of claim 7, wherein said solid salt dosage form is transrectally inserted into said prostate tissue under real-time ultrasonic observation and wherein said salt is potassium chloride, or sodium chloride, or a combination thereof.

19. The method of claim 18, wherein said salt dosage form includes sodium chloride.

20. The method of claim 1, wherein said solid salt dosage form is inserted into said prostate tissue by an apparatus comprising: (a) a shaft comprising a longitudinal lumen; (b) a magazine adapted to hold a plurality of said dosage forms, said magazine comprising an outlet; and (c) a pushing member for pushing said dosage forms from a position proximate said magazine outlet, through said lumen of said shaft and into said tissue.

21. The method of claim 20, wherein said shaft is flexible and adapted for penetration of said tissue.

22. The method of claim 20, wherein said shaft is rigid and adapted for penetration of said tissue.

23. The method of claim 20, wherein said pushing member is adapted for penetration into said tissue.

24. The method of claim 20, wherein said tissue is prostate tissue.

25. The method of claim 20, wherein said apparatus further comprises an ultrasound probe.

26. A system for the chemical ablation of prostate tissue, said system comprising: (a) at least one solid salt dosage form comprising 50-100% w/w salt; and (b) an apparatus for inserting said solid salt dosage form into said tissue, said apparatus comprising a sharpened shaft having a longitudinal lumen and a pushing member configured to advance the dosage form through the lumen and into prostate tissue.

* * * * *